United States Patent
Rong et al.

(10) Patent No.: US 6,475,770 B1
(45) Date of Patent: Nov. 5, 2002

(54) PROCESSES FOR PREPARATION OF MAREK'S DISEASE USING CONTINUOUS MAMMALIAN CELL LINES

(75) Inventors: Sing Rong, Old Lyme; Michael G. Sheppard, North Stonington, both of CT (US)

(73) Assignee: Pfizer, Inc., New York, NY (US)

(*) Notice: Subject to any disclaimer, the term of this patent is extended or adjusted under 35 U.S.C. 154(b) by 0 days.

(21) Appl. No.: 09/587,835

(22) Filed: Jun. 6, 2000

Related U.S. Application Data (63) Continuation of application No. 09/208,347, filed on Dec. 9, 1998, now abandoned, which is a continuation-in-part of application No. 09/094,368, filed on Jun. 9, 1998, now abandoned.
(60) Provisional application No. 60/049,055, filed on Jun. 10, 1997.

(51) Int. Cl.$^7$ .................. C12N 15/869; C12N 7/00; C12N 7/01; C12N 5/10; A61K 39/255

(52) U.S. Cl. .................. 435/235.1; 435/320.1; 435/325; 435/351; 435/455; 435/456; 435/236; 435/239; 435/91.4; 435/91.41; 435/91.42; 424/93.1; 424/93.2; 424/93.6; 424/186.1; 424/199.1; 424/204.1; 424/209.1; 424/211.1; 424/214.1; 424/229.1

(58) Field of Search .................. 435/235.1, 320.1, 435/325, 351, 455, 456, 236, 239; 424/93.1, 93.2, 93.6, 186.1, 199.1, 204.1, 209.1, 211.1, 214.1, 229.1

(56) References Cited

U.S. PATENT DOCUMENTS

| | | | | |
|---|---|---|---|---|
| 5,558,867 A | * | 9/1996 | Sakaguchi et al. | 424/199.1 |
| 5,928,913 A | * | 7/1999 | Efstathiou et al. | 435/172.3 |

FOREIGN PATENT DOCUMENTS

| | | |
|---|---|---|
| NZ | 243251 | 11/1993 |
| NZ | 242707 | 3/1994 |

OTHER PUBLICATIONS

Kunihiko Fukuchi, et al.; Structure of Marek's Disease Virus DNA: Detailed Restriction Enzyme Map; J. of Virology; (1984); vol. 51, No. 1; pp. 102–109.

K. Venugopal, et al.; Molecular Pathogenesis of Marek's Disease—Recent Developments; Avian Pathology; (1995); vol. 24; pp. 597–609.

V. Zelnik; Marek's Disease and New Approaches to its Control; Acta Virologica; (1995); vol. 39; pp. 53–63.

Hajime Ogura, et al.; Establishment and Characterization of a Virus–free Chick Cell Line; Acta Med. Okayama; (1987); vol. 43, No. 3; pp. 141–143.

Mark S. Parcells, et al.; Characterization of Marek's Disease Virus Insertion and Deletion Mutants that Lack US1 (ICP22 Homolog), US10, and/or US2 and Neighboring Short–Component Open Reading Frames; J. of Virology; (1994); vol. 68, No. 12; pp. 8239–8253.

Mark S. Parcells, et al.; Retention of Oncogenicity by a Marek's Disease Virus Mutant Lacking Six Unique Short Region Genes; J. of Virology; (1995); vol. 69, No. 12; pp. 7888–7898.

S. K. Reddy, et al.; Protective Efficacy of a Recombinant Herpesvirus of Turkeys as an in ovo Vaccine against Newcastle and Marek's Disease in Specific–pathogen–free Chickens; Elsevier Science Ltd.; (1996); vol. 14, No. 6; pp. 569–477.

Mark S. Parcells, et al.; Characterization of a Marek's Disease Virus Mutant Containing a LacZ Insertion in the US6 (gD) Homologue gene; Virus Genes: (1994); vol. 9.1; pp. 5–13.

Vladimir Zelnik, et al.; Characterization of Proteins encoded by the Short Unique Region of Herpesvirus of Turkeys by in vitro Expression; J. of General Virology; (1994); vol. 75; pp. 2747–2753.

Robert Isfort; Retrovirus Insertion into Herpesvirus in vitro and in vivo; Proc. Natl. Acad. Sci.; (1992); vol. 89; pp. 991–995.

R. F. Silva, et al.; Recombinant Viruses as Poultry Vaccines; (1990); vol. 41, pp. 153–162.

K. Nazerian, et al.; Protection and Synergism by Recombinant Fowl Pox Vaccines Expressing Genes from Marek's Disease Virus; Avian Diseases; (1996); vol. 40; pp. 368–376.

Yukio Utsui, et al,; In Vitro and in Vivo Antibacterial Activities of CS–807, A New Oral Cephalosporin; Antimicrobial Agents and Chemotherapy; (1987); vol. 31, No. 7; pp. 1085–1092.

John H. Bateson, et al.; Novel C–3 Cyclic Ether Cephalosporins and their Orally Absorbed Prodrug Esters; (1993); vol. 47, No. 2; pp. 253–256.

Koichi Fujimoto, et al.; Studies on Orally Active Cephalosporin Esters; The Journal of Antibiotics; (1986); vol. XL, No. 3; pp. 370–384.

Vladimir Zelnik; Structure and properties of a herpesvirus of turkeys recombinant in which US1, US10 and SORF3 genes have been replaced by a lacZ Expression Cassette; J. of General Virology; (1995); vol. 76; pp. 2903–2907.

(List continued on next page.)

Primary Examiner—David Guzo
(74) Attorney, Agent, or Firm—Scully, Scott, Murphy & Presser (57) ABSTRACT

The present invention relates to mammalian cell lines which efficiently support the growth and productive infection of Marek's Disease Virus at high titers. The present invention also relates to mammalian cell lines which have been engineered to support the growth and productive infection of recombinant Marek's Disease Virus at high titers. The present invention relates a process for the preparation of Marek's Disease Virus in quantities suitable for vaccine purposes.

3 Claims, 3 Drawing Sheets

OTHER PUBLICATIONS

Robin W. Morgan; Protection of Chickens for Newcastle and Marek's Disease with a Recombinant Herpesvirus of Turkeys Vaccine Expressing the Newcastle Disease Virus Fusion Protein; Avian Diseases; (1992); vol. 36; pp. 858–870.

R. L. Witter, et al.; Pathogenicity of Variant Marek's Disease Virus Isolants in Vaccinated and Unvaccinated Chickens; Avian Diseases; (1979); vol. 24, No. 1; pp. 210–232.

K. Nazerian; An Updated List of Avian Cell Lines and transplantable Tumours; Avian Pathology; (1987); vol. 16; pp. 527–544.

Hajime Ogura, et al.; Establishment and Characterization of a Virus–free Chick Cell Line; Acta Med. Okayama; (1987); vol. 41, No. 3; pp. 141–143.

Mitsuru Ono, et al.; Preparation of monoclonal Antibodies against Marek's Disease Virus Serotype 1 glycoprotein D Expressed by a Recombinant Baculovirus; Virus Research; (1995); vol. 38; pp. 219–230.

R.L. Witter, et al.; Studies on the In Vivo Replication of Turkey Herpesvirus; J. of the National Cancer Institute; (1972); vol. 49; pp. 1121–1129.

B.W. Calnek, et al.; A Source of Enveloped and Infectious Cell–Free Herpesvirus from Marek's Disease; Dept. of Avian Diseases and Microbiology; (1969); pp. 219–233.

R. Shek, et al.; Characterization of Marek's Disease Virus-–Infected Lymphocytes: Discrimination Between Cytolytically and Latently Infected Cells; JNCL; (1983); vol. 70, No. 3; pp. 485–491.

Yoko Akiyama, et al.; Continuous Cell Culture from Lymphoma of Marek's Disease; Biken Journal; (1973); vol. 16; pp. 177–179.

Yoko Akiyama, et al.; Two Cell Lines from Lymphomas of Marek's Disease; Biken Journal ; (1974); vol. 17, No. 3; pp. 105–116.

Powell, P.C., et al.; T lymphoblastoid Cell Lines from Marek's Disease lymphomas; Nature; (1974); vol. 251; pp. 7–8.

B.W. Calnek; Establishment of Marek's Disease Lymphoblastoid Cell Lines from Transplantable Versus Primary Lymphomas; Int. J. Cancer; (1978); vol. 21; pp. 100–107.

L.N. Payne, et al.; Use of an Agar Culture Technique for Establishing Lymphoid Cell Lines From Marek's Disease Lymphomas; Int. J. Cancer; (1981); vol. 28; pp. 757–766.

K. Nazerian, et al.; Properties of a Chicken Lymphoblastoid Cell Line From Marek's Disease Tumor; J. of the National Cancer Institute; (1975); vol. 54, No. 2; pp. 453–458.

Henri–Jacques Delecluse; Status of Marek's Disease Virus in Established Lymphoma Cell Lines: Herpesvirus Integration Is Common; J. of Virology; (1993); vol. 67, No. 1; pp. 82–92.

Taiseer Maray, et al.; TNA Transcript of Marek's Disease Virus (MDV) Serotype–1 in Infected and Transformed Cells; Virus Gene; (1988); vol. 2:1; pp. 49–68.

Keizo Sugaya, et al.; Latent Transcripts of Marek's Disease Virus Are Clustered in the Short and Long Repeat Regions; J. of Virology; (1990); vol. 64, No. 12; pp. 5773–5782.

K.A. Schat, et al.; Partial Transcription Map of Marek's Disease Herpesvirus in Lytically Infected Cells and Lymphoblastoid Cell Lines; Int. J. of Cancer; (1989); vol. 44; pp. 101–109.

K. Nazerian, et al.; A Nonproducer T Lymphoblastoid Cell Line from Marek's Disease Transplantable Tumor (JMV); Avian Diseases; (1977); vol. 21, No. 1; pp. 70–75.

R.L. Witter; Protection by Attenuated and Polyvalent Vaccines against highly Virulent Strains of Marek's Disease Virus; Avian Pathology; (1982); vol. 11; pp. 49–62.

R.L. Witter, et al.; Polyvalent Marek's Disease Vaccines: Safety, Efficacy and Protective Synergism in Chickens with Maternal Antibodies; Avian Pathology; (1984); vol. 13; pp. 75–92.

R.L. Witter; Principles of Vaccination; L.N. Payne (ed); (1985); pp. 203–250.

K. Kazerian; An Updated List of Avian Cell Lines and Transplantable Tumours; Avin Pathology; (1987); vol. 16; pp. 527–544.

A.E. Churchill; Production of Vaccines; L.N. Payne (ed); (1985); pp. 251–265.

Carol Glaubiger, et al.; Marek's Disease Herpesviruses IV. Molecular Characterization of Marek's Disease Herpesvirus A Antigen; J. of Virology; (1983); vol. 45, No. 3; pp. 1228–1234.

Paul M. Coussens, et al.; Structure and Complete Nucleotide Sequence of the Marek's Disease Herpesvirus gp67–65 Gene; J. of Virology; (1988); vol. 62, No. 7; pp. 2373–2379.

Hajime Ogura, et al.; Establishment and Characterization of a Virus–free Chick Cell Line; Acta Med. Okayama; (1987); vol. 41; pp. 141–143.

Zhizhong Cui, et al.; Structural Analysis and Transcriptional Mapping of the Marek's Disease Virus Gene Encoding pp38, an Antigen Associated with Transformed Cells; J. of Virology; (1991); vol. 65, No. 12; pp. 6509–6515.

Yu Hong, et al.; Identification of an Immediate–Early Gene in the Marek's Disease Virus Long Internal repeat Region Which Encodes a Unique 14–Kilodalton Polypeptide; J. of Virology; (1994); vol. 68, No. 6; pp. 3593–3603.

Partial Filling of Recessed 3' Termini of Fragments of Genomic DNA; Analysis and Cloning of Eukaryotic Genomic DNA; pp. 9.29–9.62.

* cited by examiner

SEQUENCE LISTING

<160> NUMBER OF SEQ ID NOS: 12

<210> SEQ ID NO 1
<211> LENGTH: 2023
<212> TYPE: DNA
<213> ORGANISM: Marek's disease virus

<400> SEQUENCE: 1

```
acggtctctg aacaagacgg gcgataatat tagccatgtt tcgcatagcc gtacctcccg      60
ttctctcctg attatttgaa aatgataaag tagccgtttt attacaagct atatgattcc     120
tcaaatccgt tacgttagca gacgcctttc cactgcgtcg ttgtatatgt atcgtgtttg     180
tattatgacg ttttaaaatt ttatgagtgt cagttatccg tgctttatag tcagacgcgg     240
tcgccaatat agagcatagt ctatgaaaat cagtcactat gtgccttttc tttaggcaca     300
tcacatgtag aacagacagt tttcgtcttg ctacaaatac taacattgga caaataacga     360
tacaatctga tccttgaggc gcaatttgcc caatcagaga tttggaatcc ataactgct     420
ttatgccggt gagtctttgt tcatgtttac tgcgtgtctt caggttacga gaaaatttgc     480
aagttttag ttctagaatg acgcatactc catcacagcc tacttccac aaatcacgag      540
gcaacttaaa catgcaaata caatccggtc tacgtcgttc taggtttact cgaagacca     600
atcgaaaatc cgtcaactgt ttaaatacat ctaataccat gaccttccca aaaattttgg     660
caaagcttct cccggccaa tcatacacct gagatcctag acacatcgct tctgcataaa     720
gccgtttgta aaagcgatcg tgacatcgaa caccagccgc taaacgtcgc tttctaagga     780
cattcgtatt tacatgccgt ttgaaatttc gagtgctact aacctgtctg cgatatcttt     840
tgagtacgtt cttctctccc attgaacatg tcggagccac aatcgtggtc ggtaatgca     900
tctcagatga catctgcaca gctcatacgt gtataacctcg atggatcaat gggtataggt    960
aaaacgtcaa tgttgaatga gataccgacg cactctttaa tgggagtacc cgtactaaag   1020
gttttcgaac ctatgaaata ctggcggtat tatttttactg atttggtcac gaccgtaaat   1080
gatacatgtg atcgtcgtcg caggggagag ttttctttat ttcaatctag catgattgta   1140
acagctttac aatcaaagtt tgcagatccc tatcttgtat ttcatgagcg cttatcgtcg   1200
aagtgtcatc gcataacagg aacacgtggc aatccatcgc ttatattaat tctagatcga   1260
catcccatat ccgctaccgt atgttttccc attgctcgac atttaactgg agattgttcc   1320
ttggagatgc taattagtat gataataagg ttgccccagg aaccgccagg atgcaacttg   1380
gtgattgtcg atctacatga cgaaaaggag catgttagcc gtctatcttc acggaatagg   1440
accggcgaga aaacagatct actaatgctc agggcactta atgcagtgta ttcctgttta   1500
gtagacacta ttatgtacgc aaatcatatt tgtccctaca gtaaggatga atgggaatct   1560
gaatggttgg atctaccatg gtttgataca tctttggcca caacgtttat aaacgaacct   1620
cgtactgatt atcgcggtag tagggtgtca ttacaccata cgcttttagc gatatttaag   1680
cggcgagaat tatgtgccga agatggtagc ttatcaacaa cgcatgcatg gatattgtgg   1740
ggattattaa tgaaactgcg gaacattaac gtcgaacgat ttaatattac tggcctgtcc   1800
acaacaaagt gtgtagaatc gttcatggat actatgtcgg agagattggt aacacatagt   1860
agctggaatg atgccttcga gattgaagct gatgtactag cctataataa agagatggct   1920
```

```
atgtaaaact acccattcat atcgcgcttc tataattagc ttgcccacat cacaatgatg   1980
cggcaatatt gacttatatt aagatagtaa tttggcgtcc tta                    2023
```

<210> SEQ ID NO 2
<211> LENGTH: 2236
<212> TYPE: DNA
<213> ORGANISM: Marek's disease virus

<400> SEQUENCE: 2

```
taaataaaga actttgggaa taacaagcta tgtatagaat ttatttcgcg tgaagatttt     60
tcccaagtcc gatcacattt caggtattac agcggtaata gatccatgca ttatgagggt    120
ttgacgtatt atctcgatta agaacatatt gtaatacacc cactgtttct caaacgagtg    180
tctatcaatg atataataca ttgatgtatc gactataata cccccaatgt tcaaaggctg    240
ataaaactga tatatctatg gccgcgcata gcaattctgc cgtatcttct ccaccgatt     300 ctcgtaacgc gacgtctatg ggatcaatgt ctttatatag accgtctaga ataagagcca    360
gtttacgtat cttgaggtcc tgtatagatt ttggtgcaga tgtttctgcc acatccaata    420
aagtagtctc gtctgcaaag gctgatggac taagaactcc atgttgctct tccaatgaag    480
aagtccagtt cacaactaat ttcagtaacc atgccaagaa ataaaatcct ctgaataaac    540
tgtttgtttc tgcaagacaa gtcggcatgg agtaggcatt cccctcaat ggtagaggta     600 tgatgatcgc acaactcgcg aattaagtca taacaatttg gcagacgatt taatatatgt    660
atatactgaa gcaacaaaaa cttctgactg ggcgatatat ttttgttttc tggtccaact    720
ccaacaaaca tggatgcgtg tcttccaaat aaagcatttg aaatcatccc caactccactt   780 tgtataattt ccaggtcgga ttgagatcca ttctccgtat aagattagaa tttaaattga    840
gcatgttcat attaaaaacc gagtctactt tccagaagat ttcccataac ttatttagag    900
aagtagaggg tatacaagag ctggtatcgc aactccatat cttaaatacg ggtggtatat    960
atttgatttg taccaagaa ctgaaccgag catgttttt ccgttgtact ggatttgttt     1020
gttactgttc acgttcaatt taccccggct ccagccgtca tatcccatgc gcgttgcaca   1080
gtcgtcgtgt ttgcagcttt cttgtctgta actataacat cgactcgcct gccgaatatc   1140
tctgatgata atgcttctct aggagtggga atgccatcaa ataatccttc aacgaggtca   1200
ctcaaagact taggtaattc agtcaatctt gcacaagtta gcacaaatgc atcacgactg   1260
cactcatata ctaaatctga atatatgtcc gtgattatag ggaattcggg tatatgaatt   1320
gtacgatcat gtggaaaatc gtatgcggcc tgtatcgtta acccagaaat tgcatttgtc   1380
ggtaccatat actttgctat atccggatca tacgtttcca gacagagaag cccacaaagc   1440
tcacgttcac tgcatatacc atcacgactt aacacagcta tactatcgat gaacaattca   1500
tcttcatcgg aagaaaaagc ccacttcata cctctgcgaa gtaattctcg gcgaacatga   1560
gctgccaatg gtttggactg accaccacgt agaaccaacc caattttttgc gagctctggt   1620 aataccatca tctatacagc ctgcctacag caaaaaacaa ccgccgcaaa aaatacctt    1680 tatatcccat tccgatacat aaaactggac attctataac gaaaacatgt ccgtatttaa   1740
tatccattga ctgtcctctc tggacgtaac ctatatcact gtagcgcaaa tccaatcctt   1800
gataacagca ttgcgttaat cactgggtgc acggattaac gtgtacgtat ttactgtcgc   1860
gtcatatgaa cgacaatgag cttgggtatg cagctcgtca ttgaacgcca tttgtggcaa   1920
agcaataagg gtctcagacc atcacattat tcgacgaatt gtactacata ggccaccct    1980
```

-continued

```
tgtttaacta tgtcaagcat ggatttggat actatgtcaa cagaagctaa tgaatatacc      2040
atccccctca tgaattgatg atggacgatc ggatacatgc gaaaactctt gggtcgtatt      2100
gaccactatc tgaggaatta gattgggatg atattatgca ctttctctta tttaggcgat      2160
atattttaca atccaacagc tatgacatac atcctcaaat cacccgtatg tttactcttt      2220
ggctatctac tttgtc                                                     2236

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 3
gggggtacca agtgcattgg atggctacat a                                      31

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence:Primer

<400> SEQUENCE: 4
ggggctagct taaagatcgt cgtacaggct caa                                    33

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 5
aagatttttc ccaagtcc                                                     18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 6
tcgtcgaata atgtgatc                                                     18

<210> SEQ ID NO 7
<211> LENGTH: 59
<212> TYPE: DNA
<213> ORGANISM: Artificial Sequence
<220> FEATURE:
<223> OTHER INFORMATION: Description of Artificial Sequence:pCR 3.1
       vector

<400> SEQUENCE: 7
taatacgact cactataggg agacccaagc tggctagcgt ttaaacttaa gcttggtac        59

<210> SEQ ID NO 8
<211> LENGTH: 54
<212> TYPE: DNA
<213> ORGANISM: Artificial Sequence
<220> FEATURE:
<223> OTHER INFORMATION: Description of Artificial Sequence:pCR 3.1
       vector
```

```
<400> SEQUENCE: 8
tcgagtctag agggcccgtt taaacccgct gatcagcctc gactgtgcct tcta        54

<210> SEQ ID NO 9
<211> LENGTH: 59
<212> TYPE: DNA
<213> ORGANISM: Artificial Sequence
<220> FEATURE:
<223> OTHER INFORMATION: Description of Artificial Sequence:T7
      promoter/priming site (upper)

<400> SEQUENCE: 9
taatacgact cactataggg agacccaagc tggctagcgt ttaaacttaa gcttggtac   59

<210> SEQ ID NO 10
<211> LENGTH: 55
<212> TYPE: DNA
<213> ORGANISM: Artificial Sequence
<220> FEATURE:
<223> OTHER INFORMATION: Description of Artificial Sequence:T7
      promoter/priming site (lower)

<400> SEQUENCE: 10
attatgctga gtgatatccc tctgggttcg accgatcgca aatttgaatt cgaac       55

<210> SEQ ID NO 11
<211> LENGTH: 54
<212> TYPE: DNA
<213> ORGANISM: Artificial Sequence
<220> FEATURE:
<223> OTHER INFORMATION: Description of Artificial Sequence:pCRr3.1
      reverse priming site (upper)

<400> SEQUENCE: 11
tcgagtctag agggcccgtt taaacccgct gatcagcctc gactgtgcct tcta        54

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence:pCRr3.1
      reverse priming site (lower)

<400> SEQUENCE: 12
cagatctccc gggcaaattt gggcgactag tcggagctga cacggaagat             50
```

PROCESSES FOR PREPARATION OF MAREK'S DISEASE USING CONTINUOUS MAMMALIAN CELL LINES

CROSS-REFERENCE TO RELATED APPLICATIONS

This application claims benefit from U.S. Provisional Application Ser. No. 60/049,055, filed Jun. 10, 1997. This application is a continuation-in-part from U.S. application Ser. No. 09/094,368, filed Jun. 9, 1998 now abandoned, and continuation of U.S. application Ser. No. 09/208,347, filed Dec. 9, 1998.

The present invention relates to the use of continuous mammalian cell lines that support the growth and productive infection of Marek's Disease Virus (MDV) at high titers. The present invention relates to a cell line that can be used as a substrate to efficiently propagate large quantities of Marek's Disease Virus, in particular, for vaccine production. The present invention relates to recombinant Marek's Disease Virus vectors and cell lines to package said vectors and recombinant Marek's disease viruses which may be used as vaccines. Marek's Disease Virus vectors and vaccines may be used to protect avians from infection with Marek's Disease Virus and against disease resulting from infection.

BACKGROUND OF THE INVENTION

Marek's Disease (MD) is an acutely oncogenic disease of chickens, which causes lymphomas, visceral tumors, nerve lesions and immunosuppression. The disease is global and ubiquitous in distribution. The etiologic agent is herpesvirus, Marek's Disease Virus. Marek's Disease has been a primary cause of deaths and condemnations in broiler flocks [Calnek, B. W. and Witter, R. L., Diseases of Poultry, 9th edition, Iowa State Press, Ames, Iowa, pp. 342–385 (1991)].

There are three serotypes of Marek's Disease Virus. Serotype 1 includes all pathogenic strains and their attenuated derivatives. Serotype 2 consists of naturally avirulent chicken viruses, while serotype 3, also known as Herpesvirus of Turkeys (HVT), includes avirulent turkey viruses that are capable of replication in chickens. The three serotypes are partially cross-protective, but can be distinguished using monoclonal antibodies [Silva, R. F. and Lee, L. F., Virol. vol. 36. pp. 307–320 (1984)] and other known methods.

Marek's Disease Virus appears to be less recombinogenic than other herpes viruses, and the cell-associated nature of the virus makes plaque purification of recombinants away from parental virus problematic. Nevertheless, recombinant MD viruses have been generated from serotype 1 [Sonoda, K. et al., Vaccine V. 14, pp. 277–284 (1996); Parcells, M. S., et al., J. Virol., V. 69. pp. 7888–7898 (1995); Parcells M. S., et al., Virus Genes, V. 9, pp. 5–13, (1994); Parcel M. S., et al., J. Virol., V. 68, pp. 8239–8253 (1994); Sakaguchi, M., Vaccine V. 12, pp. 953–957 (1994); Reddy, S. K., et al., Vaccine V. 14, pp. 469–477 (1996)], serotype 2 [Marshall, D. R., et al., Virol. V. 195, pp. 638–648 (1993); Silva, R. F., 14th International Herpesvirus Workshop (Abstract) (1989)]; and serotype 3 [Reddy, S. K., et al., Vaccine V. 14, pp. 469–477 (1996); PCT Parent Application WO 95/29248 (1995); Silva, R. F., 14th International Herpesvirus Workshop (Abstract) (1989); Darteil, R., et al., Virol. V. 211, pp. 481–490 (1995); U.S. Pat. No. 5,187,087 issued in 1995; Zelnik, V., et al., J. Gen. Virol. V. 76, pp. 2903–2907 (1995); PCT Patent Application WO 93/25665, published (1993); Ross, L. J. N., et al., J. Gen. Virol., V. 74, pp. 371–377 (1993), Sondermeijer, P. J. A., et al., Vaccine V. 11, pp. 349–358 (1993); European Patent No. 431,668 B1, published (1995); Morgan, R. W., et al., Avian Dis., V. 36, pp. 858–870 (1992); Bandyopadhyay, P. K., et al., 13th International Herpesvirus Workshop 323 (Abstract) (1988)]. In all of the above mentioned references, the viruses were replication competent and were produced in primary avian cells.

Commercially available Marek's Disease Virus vaccines, with the exception of some monovalent HVT formulations, consist largely of live Marek's Disease Virus-infected primary chicken embryo fibroblast (CEF) cells. A significant problem associated with using whole live Marek's Disease Virus-infected primary chicken cells to grow Marek's Disease Virus for use in vaccines is that the CEF cells must be stored at liquid nitrogen temperatures and administered by injection in order to be effective. Whole live cell vaccines have been previously necessary since the three Marek's Disease Virus serotypes are strongly cell-associated in cell culture and in most tissues of an infected bird. Spread of infection within birds can be achieved by direct cell to cell contact, with little or no cell-free virus being released. Infectious virions are produced only in the feather follicle epithelium (FFE), and are responsible for bird-to-bird transmission [Calnek, B. W., et al., Avian Dis., V. 14, pp. 219–233 (1970); Witter, R. L., et al., J. Natl. Cancer Inst., V. 49, pp. 1121–1130 (1972); Edison, C. S., et al., J. Natl. Cancer Inst., V. 47, pp. 113–120 (1971)].

Commercial cell-free Marek's Disease Virus vaccines can be made by cell culture. However, the production of cell-free Marek's Disease Virus vaccines has been thus far been limited to vaccines produced using only serotype 3 Marek's Disease Virus. This is because only serotype 3 Marek's Disease Virus makes free virions in sufficient quantities for production of Marek's Disease Virus vaccines. It has been suggested that lack of expression of the viral glycoprotein D (gD) gene may be involved in limiting release of cell-free virions [PCT Patent Application WO 95/29248 published (1995); Tan, X. and Velicer, L. F., 18th International Herpesvirus Workshop A, 145 (Abstract) (1993)].

In addition to CEF, other primary avian cells have been used to grow Marek's Disease Virus, including chicken embryo kidney (CEK) and duck embryo fibroblast (DEF). Only two continuous avian cell lines have been described as being capable of growing certain Marek's Disease Virus serdtypes. Serotype 3 Marek's Disease Virus (Marek's Disease Virus-3) has been described as growing on a chemically transformed quail cell line designated QT35 [Nikura, M., Nanta, T. et al., J. Vet. Med. Sci., V. 53, pp. 439–446 (1991)]. A chemically transformed CEF cell line designated CHCC-OU2 [Ogura, H. and Fujiwara, T., Acta Med. Okayama, V. 41, pp. 141–143 (1987)] has been described as supporting the growth of Marek's Disease Virus-1 [Abujoub, A. and Coussens, P. M., Virol., V. 214, pp. 541–549 (1985)].

Other known processes for producing Marek's Disease Virus include the use of tumorigenic or oncogenic cell lines. Marek's Disease Virus-transformed lymphoblastoid cell lines [Nazerian, K. Avian Pathol. V. 16, pp. 527–544 (1987)] are derived from lymphoid tumors in chickens infected with oncogenic Marek's Disease Virus-1. The viral genome is maintained in a latent or semi-latent state in these cells, such that transmission of infection to co-cultivated CEF cells or DEF cells occurs at a low frequency, if at all. In addition, these lymphoblastoid lines are refractory to superinfection with other Marek's Disease Virus viruses. Furthermore, Marek's Disease Virus-transformed lymphoblastoid cell lines have not demonstrated utility in the production of nonrecombinant (conventional) Marek's Disease Virus vaccines or in the preparation of recombinant Marek's Disease Virus viruses or genetically altered Marek's Disease Virus viruses or vectors.

Similarly, lymphoblastoid cell lines [Nazerian, K., Avian Pathol., V. 16, pp. 527–544 (1987)] derived from oncogenic avian retroviruses (avian leukosis virus and reticuloendotheliosis virus) are not useful for the production of commercial Marek's Disease Virus vaccines or for the generation of recombinant Marek's Disease Virus, due to the shedding of retroviruses, the poor growth characteristics of lymphoblastoid cells, and the low level of productive Marek's Disease Virus infection.

Mammalian primary cells and mammalian cell lines have never been described as suitable substrates for the growth of any serotype of Marek's Disease Virus, nor has any mammal ever been demonstrated to be productively infected with Marek's Disease Virus.

SUMMARY OF THE INVENTION

The present invention relates to mammalian cell lines that efficiently support the growth and productive infection of Marek's Disease Virus (MDV) at high titers. The present invention also relates to mammalian cell lines that have been engineered to support the growth and productive infection of both naturally occurring and recombinant Marek's Disease Virus at high titers. The present invention relates to a process for the preparation of Marek's Disease Virus in quantities suitable for vaccine purposes.

The present invention is based, in part, on the discovery of continuous cell lines that support the growth and productive infection of Marek's Disease Virus at high titers. In particular, it has been discovered that the mammalian cell line that supports the growth of Marek's Disease Virus at high titers is a feline kidney cell line.

In accordance with the present invention, the term 'MDV' refers to an MDV viral particle that corresponds to a naturally occurring MDV viral particle, e.g., a wildtype MDV or a naturally occurring mutant MDV, or a recombinant MDV viral particle. A naturally occurring MDV viral particle is encoded by a wildtype MDV genome or the genome of a naturally occurring MDV. A recombinant MDV viral particle is encoded by a recombinant MDV genome. A recombinant MDV genome comprises the nucleotide sequences of the MDV genome or a fragment thereof. Such fragment must be of sufficient length so as to encode at least one MDV gene product or a fragment of such gene product such that the fragment of the gene product retains the activity of the gene. For example, the recombinant MDV genome comprises the nucleotide sequence of MDV that has been deleted of a gene(s) whose gene product is essential for viral replication or some other state of the viral life cycle. In addition, a recombinant MDV genome can further comprise a nucleotide sequence that encodes a heterologous gene or a heterologous fragment. Such fragment comprises nucleotide sequences encoding an antigenic epitope, a regulatory sequence, or a fragment of a gene that still retains a sufficient fragment such that the polypeptide encoded by such fragment retains the activity of the gene product.

The present invention also encompasses a continuous mammalian cell line that contains DNA encoding the naturally occurring MDV or a recombinant MDV, e.g., the nucleotide sequence of MDV that has been deleted of a gene or fragment thereof which gene product is essential for viral replication or some other stage of the viral life cycle. In yet another embodiment, the present invention encompasses continuous mammalian cell lines that contain nucleotide sequences encoding recombinant MDV such as, DNA encoding a MDV gene or fragment thereof which is essential for viral replication or some other stage of the viral life cycle. Such nucleotide sequences may be expressed constitutively or transiently under the control of the cell's own regulatory elements or heterologous regulatory elements.

The present invention further encompasses continuous mammalian cell lines that are engineered to stably express the nucleotide sequences of naturally occurring MDV or recombinant MDV, either under the control of constitutively active regulatory elements or inducible regulatory elements.

The present invention also encompasses continuous mammalian cell lines that are infected with naturally occurring MDV or recombinant MDV, cells expressing MDV or a cell lysate or components of cells infected with MDV.

The MDV may be selected from the group consisting of serotype 1, serotype 2, serotype 3, taken singly or in any combination thereof.

In another aspect, the invention relates to the use of MDV for the preparation of a vaccine capable of inducing protection against disease in avians.

Preferably, the continuous mammalian cell line used is a feline kidney cell infected with the Md5 strain of MDV, such as cell line ATCC No. ATCC CRL-12336. Examples of other suitable strains include the MDV-1 strains 584A and 652.

The present invention also encompasses a method for propagating MDV that comprises introducing naturally occurring MDV or recombinant MDV to a continuous mammalian cell line by infecting the cell line with MDV, or cells containing MDV or cell lysates thereof, and culturing the infected cell line and harvesting cell components therefrom. The invention further encompasses formulating a vaccine from said cells or components thereof capable of inducing protection against disease in avians. The invention further encompasses formulating a vaccine from cell lysates of mammalian cell lines infected with MDV.

The present invention also encompasses a method of propagating MDV that comprises infecting a continuous mammalian cell line with DNA that encodes the nucleic acid sequence of a naturally occurring MDV or a recombinant MDV, culturing the cell line and harvesting components therefrom. In accordance with this aspect of the invention, the DNA may encode the nucleotide sequence of a naturally occurring MDV; the nudeotide sequence of recombinant MDV which comprises the nucleotide sequences of the MDV genome or a fragment thereof. Such fragment must be such that the fragment of the gene product retains the activity of the gene. In addition, the recombinant MDV may be operatively linked to a heterologous regulatory element, or may contain at least one heterologous gene or fragment.

The present invention also encompasses a continuous mammalian cell line that is transfected with DNA encoding recombinant MDV that has been deleted of a gene or fragment thereof which gene product is essential for viral replication or some other stage of the viral life cycle. In yet another embodiment, the present invention encompasses continuous mammalian cell lines that contain and express DNA encoding the MDV gene or fragment thereof which is essential for viral replication or some other stage of the viral life cycle. Such nucleotide sequences may be expressed constitutively or transiently under the control of the cell's own regulatory elements or heterologous regulatory elements. Such cell lines may be used to produce recombinant MDV by infecting and culturing such engineered mammalian cell lines with DNA encoding the nucleic acid sequence of Marek's Disease Virus. For example, the deleted gene can be one essential for replication. More particularly, the deleted gene can be the gH gene of Marek's Disease Virus or a fragment(s) thereof. In accordance with another embodiment of the present invention, second generation MDV may be produced by infecting and culturing a mammalian cell line with a cell lysate or components thereof obtained from cells infected with MDV or engineered to express MDV.

In accordance with the present invention the mammalian cell lines may be engineered to transiently express the DNA encoding naturally occurring MDV or recombinant MDV or may be engineered to stably express the DNA encoding naturally occurring MDV or recombinant MDV. In a preferred embodiment of the present invention, the mammalian cell line is a feline kidney cell line.

The MDV can be selected from the group consisting of serotype 1, serotype 2 and serotype 3, taken singly, or in any combination thereof.

In another aspect the invention relates to the above described method wherein the MDV is a virus used for the preparation of a vaccine capable of inducing protection against disease in avians.

Preferably, the continuous mammalian cell line used in the above mentioned method is a feline kidney cell line infected with the Md5 strain of MDV, such as cell line ATCC No. ATCC-CRL 12336 deposited on Apr. 8, 1997. Examples of other suitable strains include the MDV-1 strains 584A and 652. MDV-1 strain 652 may be obtained from quail myoblast cells infected with the 652 strain as deposited with the ATCC on Nov. 24, 1998, designated ATCC-12600.

The invention relates to generating a safe attenuated MDV-1 recombinant to use as a vaccine, and to generating a continuous cell line to produce the virus at high titers. In another embodiment, the present invention relates to engineering recombinant Marek's Disease Viruses and viral vectors for the use as vaccines. In yet another embodiment, the invention relates to recombinant Marek's Disease viral vectors and viruses which are engineered to encode mutant Marek's Disease viral genes or to encode combinations of genes from serotypes of Marek's Disease Virus.

The expression products and/or chimeric virions obtained may advantageously be utilized in vaccine formulations. The expression products and chimeric virions of the present invention may be engineered to create vaccines against a broad range of pathogens which afflict avians, including viral antigens. In particular, the chimeric virions of the present invention may be engineered to create anti-ALV vaccines, wherein an immunogenic polypeptide from ALV, is engineered into the genome of MDV to construct a vaccine that is able to elicit immune responses to both MDV and ALV.

The vaccine can be comprised of MDV selected from the group consisting of serotype 1, serotype 2 and serotype 3, taken either singly or in any combination thereof. Preferably, the vaccine is produced using a feline kidney cell line infected or transfected with Marek's Disease Virus.

Still another aspect of the invention is a recombinant MDV produced using the above mentioned method. The recombinant MDV can, for example, comprise the nucleic acid sequence of naturally occurring MDV from which one or more genes has been deleted, such as a gene essential for viral replication. An example of such an essential gene is the glycoprotein H (gH) gene, or fragment thereof, of the MDV genome. The resulting disabled (replication defective) virus is infectious for a single cycle provided that a complementary cell line, genetically engineered to contain the gene essential for viral replication and thereby the expression product of the deleted gene, is available to propagate the disabled virus. The production of disabled viruses and their use as vaccines is described in PCT Application GB91/01632 (Publication No. WO 92/05263), which is incorporated herein in its entirety.

Yet another aspect of the present invention is a cell line that comprises a genetically engineered mammalian cell line, that is capable of expressing a gene of naturally occurring MDV that is essential for replication, such as for example, gH, and that is capable of replication of disabled MDV virus.

Yet another aspect of the invention is a MDV vector produced using the method described above. The MDV vector comprises recombinant MDV and one or more heterologous genes or fragment(s) thereof. Optionally, the MDV vector has a 3' flanking region comprising a nucleic acid sequence as described in SEQ ID NO: 2. Also optionally, the MDV vector can have a 5' flanking region comprising a nucleic acid sequence as described in SEQ ID NO: 1. Furthermore, the MDV vector can have both a 3' flanking region comprising a nucleic acid sequence as described in SEQ ID NO: 2 and a 5' flanking region comprising a nudeic acid sequence as described in SEQ ID NO: 1.

Yet another aspect of the invention relates to a method for protecting animals against disease by administering to such animals a vaccine comprising MDV produced by the method described above. Preferably, the animal is avian.

DETAILED DESCRIPTION OF THE INVENTION

The present invention provides processes for the use of continuous mammalian cell lines for the production of naturally occurring and recombinant Marek's Disease Virus (MDV), the production of genetically engineered MDV and MDV vectors, continuous mammalian cell lines infected or transfected with MDV and vaccines capable of protecting animals against disease by MDV and/or other disease causing agents produced using such processes. Also, provided are methods of administrating MDV vaccines and MDV vector-produced vaccines to animals for protection against infection by MDV.

The preparation of the MDV vaccines of the present invention may be divided into the following stages solely for the purpose of description and not by way of limitation: (a) construction of recombinant MDV templates; (b) engineering mammalian cell lines to support productive infection of naturally occurring or recombinant MDV; and (c) rescue of MDV, cell cultures, lysates or components of lysates to be formulated as vaccines. For clarity of discussion, the invention is described in the working Examples using Md5 strain serotype 1; however, any strain or serotype of MDV may be utilized.

In accordance with the present invention, the term 'MDV' refers to an MDV viral particle that corresponds to a naturally occurring MDV viral particle, e.g., a wildtype MDV or a naturally occurring mutant MDV, or a recombinant MDV viral particle. A naturally occurring MDV viral particle is encoded by a wildtype MDV genome or the genome of a naturally occurring MDV. A recombinant MDV viral particle is encoded by a recombinant MDV genome. A recombinant MDV genome comprises the nucleotide sequences of the MDV genome or a fragment thereof. Such fragment must be of sufficient length so as to encode at least one MDV gene product or a fragment of such gene product such that the fragment of the gene product retains the activity of the gene. It is understood that recombinant MDV includes, for example, substitutions, insertions, inversions, additions, and deletions to the nucleic acid sequence of Marek's Disease Virus, and any combination thereof, such as deletion mutants of Marek's Disease Virus in which non-essential or essential regions of the MDV genome are deleted or mutated so that these regions are not expressed, e.g., gene knock outs or missense mutations. For example, the recombinant MDV genome comprises the nucleotide sequence of MDV that has been deleted of a gene(s) whose gene product is essential for viral replication or some other state of the viral life cycle. In addition, a recombinant MDV genome can further comprise a nucleotide sequence that encodes a heterologous gene or a heterologous fragment. Such fragment comprises nucleotide sequences encoding an antigenic epitope, a regulatory sequence, or a fragment of a gene that still retains a sufficient fragment such that the polypeptide encoded by such fragment retains the activity of the gene product.

The present invention encompasses recombinant Marek's Disease Virus that contains deletions and/or mutations in genes and gene regions essential for viral replication or some other stage of the viral life cycle, including initiation of infection and packaging of viral particles. In accordance with this aspect of the present invention, the deletions and/or mutations of the MDV genome are sufficient to eliminate or decrease expression of the essentional gene product and/or eliminate or decrease the activity of the essentional gene product. Examples of MDV genes that may be targeted include, but are not limited to, gH, gB, gD and the capsid gene. In accordance with this aspect of the invention, essential regions of the MDV genome are targeted in an attempt to generate a recombinant MDV with an attenuated phenotype.

Another embodiment the present invention encompasses recombinant Marek's Disease Virus that contains deletions and/or mutations in essential or non-essential regions of the MDV genome. Such regions in the MDV genome may be substituted with any heterologous nucleotide sequence to create a chimeric MDV vector. Virtually any heterologous gene sequence can be constructed into the MDV vectors for use in vaccines. In accordance with this aspect of the present invention, the heterologous gene sequence may encompass a gene product that may serve to boost or activate the host's cellular and/or humoral immune response, or a gene product that encodes an epitope that induces a protective immune response to any variety of pathogens, or antigens that bind neutralizing antibodies. For example, heterologous gene sequences that can be constructed into the chimeric vectors of the invention for use in vaccines include, but are not limited to, sequences derived from other serotypes of MDV, New Castle Disease Virus (NDV), Infectious Bursal Disease Virus (IBDV), Infectious Bronchitis Virus (IBV), Chicken Anemia Virus (CAV), Infectious Laryngotracheitis Virus (ILV), Avian Leukosis virus (ALV), Reticuloendotheliosis Virus and Avian Influenza Virus (ALV).

Insertion of a foreign gene sequence into the MDV genome can be accomplished by either a complete replacement of the viral coding region with the foreign gene or by a partial replacement. Complete replacement would probably best be accomplished through the use of PCR-directed mutagenesis. Briefly, PCR-primer A would contain, from the 5' to 3' end: a unique restriction enzyme site, such as a class its restriction enzyme site (i.e., a "shifter" enzyme; that recognizes a specific sequence but cleaves the DNA either upstream or downstream of that sequence); a stretch of nucleotides complementary to a region of the MDV gene; and a stretch of nucleotides complementary to the carboxy-terminus coding fragment of the foreign gene product. PCR-primer B would contain from the 5' to 3' end: a unique restriction enzyme site; a stretch of nucleotides complementary to a MDV gene; and a stretch of nucleotides corresponding to the 5' coding fragment of the foreign gene. After a PCR reaction using these primers with a cloned copy of the foreign gene, the product may be excised and cloned using the unique restriction sites. Digestion with the class IIS enzyme and transcription with the purified phage polymerase would generate a molecule containing the exact untranslated ends of the MDV gene with a foreign gene insertion.

It is understood that recombinant MDV includes, for example, substitutions, insertions, inversions, additions, and deletions to the nucleic acid sequence of Marek's Disease Virus, and any combination thereof, such as deletion mutants of Marek's Disease Virus in which non-essential or essential regions of the MDV genome are deleted or mutated so that these regions are not expressed, e.g., gene knock outs or missense mutations. Such variations can occur in nature or may be genetically engineered using conventional recombinant techniques to bring about such variation.

The production and manipulation of recombinant Marek's Disease Virus or fragments thereof are within the skill in the art and can be carried out according to recombinant techniques described, among other places, in Maniatis, et al., 1989, *Molecular Cloning. A Laboratory Manual*, Cold Spring Harbor Laboratory Press, Cold Spring Harbor, N.Y.; Ausubel, et al., 1989, *Current Protocols in Molecular Biology*, Greene publishing Associates and Wiley Interscience, NY; Sambrook et al., 1989, *Molecular Cloning, A Laboratory Manual*, 2d. ed., Cold Spring Harbor Laboratory Press, Cold Spring Harbor, N.Y.; Innis et al. (eds.) 1995, PCR Strategies, Academic Press, Inc., San Diego; and Erlich (ed), 1992, PCR Technology, Oxford University Press, New York, all of which are incorporated herein by reference in their entireties.

The preparation of various recombinant Marek's Disease Virus and Marek's Disease Virus vectors using recombinant techniques is known. For example, U.S. Pat. No. 5,231,023, issued Jul. 27, 1993, describes a Marek's Disease Virus Viral vector prepared by insertion of a heterologous gene into a nonessential region of the DNA genome of MDV.

The invention also encompasses the DNA expression vectors that contain any of the foregoing coding sequences operatively associated with a regulatory element that directs expression of the coding sequences and genetically engineered host cells that contain any of the foregoing coding sequences operatively associated with a regulatory element that directs the expression of the coding sequences in the host cell. As used herein, regulatory elements include, but are not limited to, inducible and non-inducible promoters, enhancers, operators and other elements known to those skilled in the art that drive and regulate expression.

The MDV genomes or fragments thereof, may be produced by recombinant DNA technology using techniques well known in the art. Methods which are well known to those skilled in the art can be used to construct expression vectors containing MDV coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding MDV gene product sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

In accordance with the present invention, the term 'MDV vector' encompasses an expression vector containing the appropriate regulatory sequences necessary for expression of one or more functional polypeptides, such as antigens. Examples of MDV vectors of the present invention include those that express the MDV genome or fragments thereof under the control of MDV regulatory elements or heterologous regulatory elements designed to enhance expression of the MDV genome in the packaging cell line.

The present invention also encompasses recombinant MDV vectors that result in virus particles with an attenuated phenotype, an example of which, is a recombinant MDV from which an essential gene has been mutated and/or deleted resulting in a replication defective MDV. The MDV genome or fragments thereof may encompass the nucleotide sequences of the naturally occurring MDV, the nucleotide sequences of genetically altered MDV or fragments thereof, including deletions of essential gene regions or the insertion of heterologous sequences. A preferred embodiment of this aspect of the invention is a recombinant MDV genome that has been deleted of the gH gene in its entirety or a large enough fragment thereof to prevent the expression of the gH gene product, or in which the gH gene has been mutated, e.g., a missense mutation so as to prevent expression of the gH gene product. Yet another preferred embodiment of this aspect of the invention encompasses is a recombinant MDV genome which has been deleted of the capsid gene in its entirety or a large enough fragment thereof to prevent the expression of the capsid gene product, or in which the capsid gene has been mutated, e.g., a missense mutation so as to prevent expression of the capsid gene product.

It is understood that MDV also encompasses recombinant MDV comprising a heterologous gene or genes incorporated into an insertion region located within the nucleic acid sequence of the genome of MDV. In a preferred embodiment of this aspect of the invention, the MDV genome is engineered to express an antigenic peptide of one or more of the three serotypes of MDV, so as to result in a multivalent vaccine to be administered to avians to confer a more complete protective effect against infection with MDV. For example, the MDV genome of a serotype 1 of MDV may be engineered to further encode the antigenic determinants of the gB gene product of serotypes MDV 2 and 3. In yet another embodiment, the heterologous genes and gene fragments may encode antigens of other avian disease causing agents. Methods for preparing recombinant Marek's Disease Virus containing heterologous genes and fragments are within the skill in the art and can be carried out according to recombinant techniques described in Maniatis et al. and other references noted above.

In yet another embodiment of the present invention, the MDV vector may be engineered to contain the nucleotide sequences of recombinant MDV and one or more heterologous genes which encode antigens for MDV or other avian disease causing agents, such as ALV. In yet another embodiment, the heterologous genes and gene fragments may encode antigens of other avian disease causing agents. In yet another embodiment, the MDV vectors of the present invention may be engineered to encode heterologous proteins which are known to boost the avian cellular immune response, thus enhancing the overall protective effect of the administered vaccine.

The MDV and heterologous genes which are engineered into the MDV vectors of the present invention may be done so using recombinant techniques within the skill of those in the art, can be expressed in the continuous mammalian cell lines of the present invention, and once formulated into an appropriate form and administered to avians elicit an immune response to both the recombinant Marek's Disease virus and/or the heterologous gene products. An adequate and functional promoter should be linked to the heterologous gene so that the MDV vector is capable of expressing the heterologous gene. The promoter may be any eucaryotic, procaryotic, or viral promoter capable of directing transcription in cells infected with the recombinant MDV vector. The preparation and use of such promoters is known and can be carried out according to recombinant techniques described in Maniatis et al., and the other references cited above.

The present invention encompasses processes for producing MDV and MDV vectors by infecting and transfecting and culturing continuous mammalian cell lines, such as for example feline kidney cells, which are capable of producing MDV or useful in the production of MDV vectors. The MDV produced in such cell lines that can then be isolated using isolation techniques known to those of skill in the art. By "infection" or "transfection" is meant the DNA transfer of virus or fragments thereof into mammalian cells. Methods for gene transfer into mammalian cells is within the skill in the art as described, for example, by Watson et al., 1992, *Recombinant DNA*, 2nd edition, W. H. Freeman and Company N.Y.

The present invention relates to continuous mammalian cell lines, in particular feline kidney cell lines, that efficiently support the growth and productive infection of Marek's Disease Virus at high titers. The present invention also encompasses continuous feline kidney cell lines that are engineered to express MDV gene products that are required for viral replication. In accordance with this aspect of the invention, such cell lines are termed "complementation cell lines" since they complement the essential viral genes and gene regions that are deleted or mutated in the recombinant MDV vectors.

The complementation cell lines of the present invention may be engineered to express any gene or gene region which has been deleted from a recombinant MDV vector. In accordance with this aspect of the invention, the cell lines may be engineered to express MDV gene products, including, but not limited to, the gH, gB, gD or capsid proteins. The cells lines may be engineered to express the MDV gene products transiently or stably under the control of constitutively active or inducible regulatory elements.

In a particularly desirable approach, cells engineered to express all MDV viral genes may result in the production of infectious chimeric virus that contains the desired genotype, thus eliminating the need for a selection system. Theoretically, one can replace any one of the genes of MDV with a foreign sequence. However, a necessary part of this equation is the ability to propagate the defective virus (defective because a normal viral gene product is missing or altered). A number of possible approaches exist to circumvent this problem. In one approach, a virus having a mutant protein can be grown in cell lines which are constricted to constitutively express the wild type version of the same protein. By this way, the cell line complements the mutation in the virus. Similar techniques may be used to construct transformed cell lines that constitutively express any of the MDV genes. These cell lines that are made to express the viral protein may be used to complement the defect in the recombinant virus and thereby propagate it. Alternatively, certain natural host range systems may be available to propagate recombinant virus, i.e., avian cell lines. A third approach to propagating the recombinant virus may involve co-cultivation with wild-type virus. This could be done by simply taking recombinant virus and co-infecting cells with this and another wild-type MDV virus (preferably a vaccine strain). The wild-type virus should complement for the defective virus gene product and allow growth of both the wild-type and recombinant virus.

For long term, high-yield production of recombinant proteins, stable expression is preferred. For example, mammalian cell lines which stably express the MDV gene products may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines.

A number of selection systems may be used, including, but not limited to, the herpes simplex virus thymidine kinase (Wigler, et al., 1977, Cell 11:223), hypoxanthine-guanine phosphoribosyltransferase (Szybalski & Szybalski, 1962, Proc. Natl. Acad. Sci. USA 48:2026), and adenine phosphoribosyltransferase (Lowy, et al., 1980, Cell 22:817) genes can be employed in $tk^-$, $hgprt^-$or $aprt^-$cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al, 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

The present invention also encompasses the continuous mammalian cell lines infected with MDV or a MDV vector. The mammalian cell line for infection or transfection with MDV is characterized as a continuous cell line free of mammalian viruses. Preferably, the mammalian cell line is a kidney cell line. These cell lines may be cultured and maintained using known mammalian cell culture techniques such as described in Celis, Julio, ed., 1994, *Cell Biology Laboratory Handbook*, Academic Press, N.Y. Various culturing conditions for these cells, including media formulations with regard to specific nutrients, oxygen, tension, carbon dioxide and reduced serum levels, can be selected and optimized by one of skill in the art.

The preferred mammalian cell line of the present invention is a feline kidney cell line. Any feline kidney cell line can be used to practice the processes of the invention, for example, feline kidney cell lines designated as CRFK, deposited on Jan. 1, 1971 with the American Type Culture Collection, 12301 Parklawn Drive, Rockville, Md. and designated ATCC CCL-94. A preferred cell line is a feline kidney cell line and any clones thereof, designated as the Norden Laboratories Feline Kidney (NLFK) cell line (Pfizer Inc.) deposited on Apr. 8, 1997 with the American Type Culture Collection, and designated as ATCC CRL-12336. The ATCC CRL-12336 cell line is a feline kidney cell line infected with the Md5 strain of Marek's Disease Virus. The Md5 strain was obtained from the American Type Culture Collection having the designation ATCC VR 987.

Mammalian cell lines, for use in the present invention can be cloned using known mammalian cell culture techniques familiar to one skilled in the art. The cells can be cultured and expanded from a single cell using commercially available culture media under known conditions suitable for propagating mammalian cells.

For example, the cell lines of the present invention kept frozen until use, can be warmed at a temperature of about 37° C. to about 38.5° C. and then added to a suitable growth medium such as OptiMEM (Life Technologies, Inc.) containing 2% fetal bovine serum (FBS). The cells can be incubated at a temperature of about 37° C. to about 38.5° C. in a humidified incubator with about 5% $CO_2$ until confluent. In order to passage the cells, the growth medium can be removed 0.05% trypsin and 0.53mM EDTA added to the cells. The cells will detach and the cell suspension can be collected into centrifuge tubes and centrifuged into cell pellets. The trypsin solution can be removed and the cell pellet resuspended into new growth medium. The cells can then be further propagated in additional growth vessels to a desired density.

In accordance with the present invention, a continuous cell line encompasses immortalized cells which can be maintained in vitro for at least about 15 to 20 passages, and can be more than 50 passages.

Infection and transfection can occur-by co-cultivation with MDV-infected cells where the MDV is non-recombinant, recombinant, genetically engineered or is an MDV vector. The cells used for co-cultivation can be MDV-infected cells such as CEF cells or DEF cells, lymphoblastoid cells, peripheral blood mononuclear cells, CHCC-OU2 cells, QT35 cells, and clones of feline kidney cells such as the 3G4 clone described in the Examples. Alternatively, mammalian cell lines may be infected with MDV by introduction of purified MDV DNA or DNA from MDV-infected cells into the mammalian cell lines using methods which are known to those of skill in the art, such as calcium phosphate coprecipitation, DEAE dextran, polybrene, lipofectin, and electroporation. Preferably, DEF or CEF MDV-infected cells are used to infect the continuous mammalian cell lines of the present invention. The cultivation of MDV-infected CEF, DEF, lymphoblastoid, peripheral blood mononuclear cells, CHCC-OU2 cells and QT35 cells are known to those of skill in the art.

For example, the mammalian cell lines can then be infected with MDV by growing the cells to about 50 to about 80% confluency, and adding DEF cells infected with MDV to the semi-confluent cells. The cells can then be incubated at a temperature of about 37 to about 38.5° C. for about 48 hours. The growth medium can then be removed and replaced with fresh medium. The cells can then be incubated for about 48 to 72 hours, preferably 48 hours, at a temperature of about 37 to 38.50° C. The medium can then be removed and replaced with medium containing 2% FBS and the cells incubated for at least 24 hours. The cells can then be split by trypsinization as described above. Infected cells can be monitored by indirect fluorescent antibody (IFA) assay using an MDV specific antibody. MDV-specific antibody can be produced using known monoclonal hybridoma techniques [Goding, James W., Monoclonal Antibodies: Principals and Practice, second edition, Academic Press (1986); Harlow et al., Antibodies, a Laboratory Manual Cold Spring Harbor Laboratory (1988)]. A frozen stock of the MDV-infected cells can then be stored until ready for use.

The present invention also relates to processes for production of vaccines comprising the MDV produced by infecting continuous cell lines, such as for example feline kidney cell lines and culturing infected cell lines to produce antigens useful as vaccines against MDV. The MDV infected cells can then be used as vaccines against MDV or the cell-free MDV isolated from the cells can be used as vaccines.

The present invention further relates to processes for producing vaccines comprising the MDV produced by transfecting or infecting continuous mammalian cell lines, such as feline kidney cell lines, with an MDV vector comprising MDV and the genes of one or more heterologous proteins or polypeptides, that is capable of expressing heterologous genes in addition to MDV, which are useful against avian disease causing agents other than MDV.

Furthermore, the invention relates to processes for producing vaccines produced by transfecting continuous mammalian cell lines with an MDV vector comprising replication-defective MDV and the genes or parts thereof of one or more heterologous proteins or polypeptides, which is capable of expressing heterologous genes in addition to MDV, which are useful against avian disease causing agents other than MDV.

Furthermore, the invention relates to processes for producing vaccines produced by transfecting continuous mammalian cell lines with an MDV vector comprising replication-defective MDV and the genes thereof of one or more heterologous proteins or polypeptides, that is capable of expressing heterologous genes in addition to MDV, which are useful against avian disease causing agents in addition to MDV, which are useful against avian disease causing agents other than MDV. Examples of other avian disease causing agents which may be useful for the production of vaccines and which are produced using the processes of the present invention include New Castle Disease Virus (NDV), Infectious Bursal Disease Virus (IBDV), Infectious Bronchitis Virus (IBV), Chicken Anemia Virus (CAV), Infectious Laryngotracheitis Virus (ILV), Avian Leukosis Virus (ALV), Reticuloendotheliosis Virus (RV) and Avian Influenza Virus (AIV) (see Fields et al. (ed.), 1991, *Fundamental Viroloqy, Second Edition*, Raven Press, New York, incorporated by reference herein in its entirety). MDV produced using the process of the present invention containing one or more heterologous proteins and polypeptides can serve as a monovalent or multivalent vaccine. Such vaccines can be prepared by methods well known to those skilled in the art of preparation of vaccines.

In accordance with the present invention, vaccine preparations comprising cell lines or components thereof, e.g., cell lysates, should be tested to ensure that the cell lines are free of other viruses and pathogens. In particular, cell lines to be formulated into vaccines to be administered to animals, such as avians, should be tested for the presence of retroviruses, such an assay can be carried out using methods known to those of skill in the art, such as a reverse transcriptase assay (Boehringer Mannheim). In addition, the cell lines may be assayed for the presence of avian pathogens using commercially available assays.

The present invention further comprises methods of administering MDV vaccines and MDV vector-produced vaccines to animal for the protection against infection with MDV. The MDV-expressing MDV and/or one or more heterologous proteins or polypeptides including those which would serve to boost the avian immune response or proteins or polypeptides of avian disease causing agents can be used to vaccinate animals, such as chickens and turkeys susceptible to such disease causing agents. Vaccination with the MDV or other antigens produced using the process of the present invention results in a protective immune response so that the inoculated animals will be protected from subsequent infection by those disease causing agents.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture.

In this regard, the use of genetically engineered MDV (vectors) for vaccine purposes may desire the presence of attenuation characteristics in these strains. The introduction of appropriate mutations (e.g., deletions) into the templates used for transfection may provide the novel viruses with attenuation characteristics. For example, specific missense mutations that are associated with temperature sensitivity or cold adaption can be made into deletion mutations. These mutations should be more stable than the point mutations associated with cold or temperature sensitive mutants and reversion frequencies should be extremely low.

Alternatively, chimeric viruses with "suicide" characteristics may be constructed. Such viruses would go through only one or a few rounds of replication within the host. When used as a vaccine, the recombinant virus would go through limited replication cycle(s) and induce a sufficient level of immune response but it would not go further in the animal host and cause disease. Recombinant viruses lacking one or more of the MDV genes or possessing mutated MDV genes would not be able to undergo successive rounds of replication. Defective viruses can be produced in cell lines which permanently express such a gene(s). Viruses lacking an essential gene(s) will be replicated in these cell lines but when administered to the animal host will not be able to complete a round of replication. In addition to non-infectious viral particles produced, such preparations may transcribe and translate—in this abortive cycle—a sufficient number of genes to induce an immune response. Alternatively, larger quantities of the strains could be administered, so that these preparations serve as inactivated (killed) virus vaccines. For inactivated vaccines, it is preferred that the heterologous gene product be expressed as a viral component, so that the gene product is associated with the virion. In yet another embodiment of the present invention, subunit vaccines comprising the antigenic determinants of MDV or heterologous viral antigenic determinants may be formulated as a vaccine. The advantage of such preparations is that they contain native proteins and do not undergo inactivation by treatment with formalin or other agents used in the manufacturing of killed virus vaccines.

In another embodiment of this aspect of the invention, inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled. The resulting vaccine is usually inoculated intramuscularly.

Inactivated viruses may be formulated with a suitable adjuvant in order to enhance the immunological response. Such adjuvants may include, but are not limited to, mineral gels, e.g., aluminum hydroxide; surface active substances such as lysolecithin, pluronic polyols, polyanions; peptides; oil emulsions; and potentially useful human adjuvants such as BCG and Corynebacterium parvum.

The cell lines and components thereof of the present invention may be formulated into the vaccine as neutral or salt forms. Pharmaceutically acceptable salts include the acid addition salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups may also be derived from inorganic bases, such as, for example, sodium potassium, ammonium, calcium, or ferric hydroxides, and such organic bases as isopropylamine, trimethylamine, 2-ethylamino ethanol, histidine, procaine and the like.

The patient to which the vaccine is administered is preferably a avian, most preferably a fowl, such as a chicken or turkey.

The vaccine formulations of the invention comprise an effective immunizing amount of the cell lines and components thereof of the present invention and a pharmaceutically acceptable carrier or excipient. Vaccine preparations comprise an effective immunizing amount of one or more antigens and a pharmaceutically acceptable carrier or excipient. Pharmaceutically acceptable carriers are well known in the art and include but are not limited to saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is preferably sterile. The formulation should suit the mode of administration.

Many methods may be used to introduce the vaccine formulations described above, these include but are not limited to oral, intradermal, intramuscular, intraperitoneal, intravenous, subcutaneous, and intranasal routes. It may be preferable to introduce the chimeric virus vaccine formulation via the natural route of infection of the pathogen for which the vaccine is designed. The immunopotency of the MDV vaccine can be determined by monitoring the immune response in test animals following immunization with the vaccine, e.g., generation of a humoral (antibody) response and/or cell-mediated immunity may be taken as an indication of an immune response. Effective doses (immunizing amounts of the vaccines of the invention may be extrapolated from dose-response curves derived from animal model test systems. The following examples further illustrate, but do not limit the present invention.

EXAMPLE 1

Propagation Of Uninfected Continuous Feline Kidney Cell Line

The feline cell line used in this work was obtained from Pfizer Animal Heath, Lincoln as Norden Laboratories Feline Kidney (NLFK) cells. Fourteen cloned cell lines were derived from parent NLFK cells by end point dilution in 96-well tissue culture plates. The cells were expanded in wells derived from a single cell. Following several passages, cells from each clone were frozen and stored at −70° C. All feline kidney cells were propagated in OptiMEM supplemented with 3% fetal bovine serum (FBS) and 22.5 µg/ml gentamicin. Monolayers of NLFK cells were maintained on OptiMEM with varying concentrations of FBS as described in the Examples below.

EXAMPLE 2

Infection Of Monolavers And Freshly Planted Cultures Of NLFK Cells

Cultures of DEF or uncloned NLFK cells in 24 well tissue culture plates were inoculated with the Md5 strain of MDV serotype 1. Preparation and propagation of DEF cells were performed as described by Solomon, J. J., Tissue Culture Association, vol. 1. pp. 7–11 (1975). Embryonated duck eggs were obtained from Cornell University.

Virus was detected with an indirect fluorescent antibody (IFA) assay using MDV-1-specific monoclonal antibodies [Silva, R. F. and Lee, L. F., Virol., vol. 36, pp. 307–320 (1984)] to glycoprotein B (1AN86) or to phosphoprotein 38 (H19). These antibodies were a generous gift of Dr. Lucy Lee of the USDA's Avian Disease and Oncology Laboratory (East Lansing. Mich.). Briefly. cells to be examined were fixed with 80% acetone, incubated with one or both monoclonal antibodies, washed and incubated with an anti-mouse FITC conjugate (Kirkegaard & Perry Laboratories). Stained cell preparations were examined with a UV microscope and positive cells were indicated by characteristic FITC fluorescence.

For positive control, an MDV seed consisted of DEF infected cells in which approximately half of the cells were expressing MDV antigen when stained by IFA. The seed was diluted to an estimated 100 IFA positive cells/well. Duplicate wells were stained periodically by IFA for the presence of MDV infection. Not all wells containing NLFK cells demonstrated the presence of replicating MDV. Only 3 out of a total of 48 wells demonstrated growth of MDV by IFA. The dilution of MDV infected DEF inoculum used in this experiments resulted in evenly distributed single cells on the bottom of a 24 well plate containing no preexisting cell monolayer. Therefore the presence of the multicell fluorescent patches indicated replication of the virus in the feline cells.

A study was conducted to determine if MDV replicated better in freshly planted cells or cells in a confluent monolayer. Monolayer cultures had been planted 4 days prior to infection. while freshly planted cells had been seeded approximately 4 hours prior to infection. The MDV infected DEF inoculum contained approximately 3000 IFA positive cells/well in a 6-well dish. As a control, inoculum only was added to several wells. The presence of MDV antigen in cells was periodically monitored by IFA staining. At 5 days following inoculation, 12 wells were trypsinized and used to plant a 75 cm$^2$ flask and additional 24 well plates. Five days later the 75 cm2 flasks and half of the wells in the 24 well plates were refed with fresh medium. The presence of MDV antigen in the 24 well plates was monitored by IFA staining at 4 days and 12 days following the initial passage. Cells from the 75 cm$^2$ flask were passaged to 24 well plates 2 days following the medium change (7 days post-passage). These cells were monitored by IFA staining five days later.

There was little difference in the ability of MDV to replicate on monolayers of NLFK cells or on freshly planted cells. Further, this experiment demonstrated that in the absence of NLFK cells, the MDV infection of DEF cells diminished and was lost by the third passage. In the presence of NLFK cells, the MDV infection is maintained and can be enhanced during passage of the infected cells. This study supports the suggestion that replication of MDV in NLFK cells is enhanced by a medium change during the infection. Both the number and the size of fluorescent foci was increased when the medium was changed at 5 days following passage.

EXAMPLE 3

Infection Of Feline Kidney Cells Cloned From NLFK Cell Line

Fifteen clones of feline cells derived from the NLFK cell line were evaluated for their ability to support growth of the Md5 isolate of MDV. The clones were grown in 75 cm$^2$ flasks. One ml of a suspension of MDV infected DEF cells containing approximately 5000 positive IFA cells was added to each flask. As controls, flasks containing the parental NLFK line or no cells were also inoculated. After 7 days, the flasks were passaged into additional 75 cm$^2$ flasks and 24 well plates. The 24 well plates were periodically monitored by IFA staining for the presence of MDV antigens in the NLFK cells. After 6 days, the flasks were refed with fresh medium. From the results of the IFA stains, the four clones showing the most aggressive MDV replication were chosen to be passaged to the next level. Eight clones showed little or no MDV spread, while the remaining three cell clones gave intermediate results Two days after the medium change these flasks were trypsinized and used to seed two 75 cm$^2$ flasks and additional 24 well plates, which were periodically monitored by IFA staining for the presence of MDV.

These results suggest that the reason uncloned NLFK cells initially demonstrated only a few positive wells is that a subpopulation of NLFK cells are capable of supporting MDV replication. Although several clones appeared to be able to support the growth of MDV to some extent, four clones demonstrated good MDV replication under the conditions used in these experiments, clones 3G4, 9, 7 and KKCL6. Clones 3G4 and 9 were the best of the four and were selected to be passaged further. It should also be noted that the DEF cell inoculum lost the MDV infection by the first passage. As noted before, medium change during incubation enhanced the spread of MDV infection.

EXAMPLE 4

Preparation of MDV-Infected Feline Kidney Cell Stocks

After several additional passages, cultures of NLFK clones 3G4 and 9 were obtained in which nearly all cells express the gB and pp38 antigens as determined by IFA. These cultures do not show the typical MDV-induced CPE seen in infected DEF cultures.

Frozen cell stocks were prepared from passages 5 and 6, and these were used as seed stock for the in vivo experiment described below.

EXAMPLE 5

Inoculation of Chickens with NLFK MDV-Infected Cells and MDV Virus

In vivo experiments were performed using specific pathogen-free chickens (strain RF1–5) obtained from Hy-Vac. CHCC-OU2 cells were used as a positive control [Ogura, H. and Fujiwara, T., Acta Med., Okayama. vol. 41. pp. 141–143, (1987)]. The very virulent MDV strain Md5 [Witter, R. L. et al., Avian Res., vol. 24, pp. 210–232. (1980)) was purchased from the American Type Culture Collection (ATCC VR-987) and was used in this study at cell culture passage level 11.

Six groups of 10 chicks each at 3 days of age were inoculated intraperitoneally with (1) a mixture of uninfected NLFK done 3G4 and NLFK clone 9 cells (cell control), (2) Md5-infected DEF cells (positive control), (3) Md5-infected OU2 cells, (4) Md5-infected NLFK clone 3G4 cells. (5) Md5-infected NLFK clone 9 cells. The remaining group (6) was an uninoculated negative control. The birds were inoculated with between 500 and 2000 TCID50 of MDV per chick. Titration of virus was determined using the TCID$_{50}$ method on monolayers of secondary DEF cells fixed with 80% acetone 6–8 days following infection and examined by IFA as described above.

Birds were necropsied if they died during the study and examined for signs of MDV infection. Kidney, spleen, liver and brain were harvested for histological evaluation from surviving birds. Blood was collected at day 14 post inoculation for virus isolation from peripheral blood lymphocytes (buffy coats) and plated on DEF cell monolayers.

All chickens injected with Md5-infected cells (groups 2–5) developed classical signs of very virulent MDV, and the majority of these birds died of MD. The negative control and cell control groups did not develop signs of MD for the duration of the experiment (8 weeks of age). The results are shown in Table 1.

TABLE 1

Numbers of surviving chicks (percentages) following challenge with MDV-1 (strain Md5), by week post-challenge

| Group | Week 1 | Week 2 | Week 3 | Week 4 | Week 5 | Week 6 | Week 7 | Week 8 | Week 9 |
|---|---|---|---|---|---|---|---|---|---|
| 1 (uninfected 3G4 and clone 9 cells) | 10/10 (100%) | 10/10 (100%) | 10/10 (100%) | 10/10 (100%) | 10/10 (100%) | 10/10 (100%) | 10/10 (100%) | 10/10 (100%) | 10/10 (100%) |
| 2 (infected DEF cells) | 10/10 (100%) | 9/10 (90%) | 9/10 (90%) | 9/10 (90%) | 8/10 (80%) | 6/10 (60%) | 5/10 (50%) | 2/10 (20%) | 1/10 (10%) |
| 3 (infected OU2 cells) | 17/17 (100%) | 17/17 (100%) | 17/17 (100%) | 17/17 (100%) | 17/17 (100%) | 17/17 (100%) | 12/17 (71%) | 10/17 (59%) | 9/17 (53%) |
| 4 (infected 3G4 cells) | 8/8 (100%) | 8/8 (100%) | 8/8 (100%) | 8/8 (100%) | 5/8 (62.5%) | 3/8 (37.5%) | 2/8 (25%) | 1/8 (12.5%) | 1/8 (12.5%) |
| 5 (infected clone 9 cells) | 10/10 (100%) | 10/10 (100%) | 10/10 (100%) | 10/10 (100%) | 10/10 (100%) | 6/10 (60%) | 4/10 (40%) | 4/10 (40%) | 3/10 (30%) |

TABLE 1-continued

Numbers of surviving chicks (percentages) following challenge with MDV-1
(strain Md5), by week post-challenge

| Group | Week 1 | Week 2 | Week 3 | Week 4 | Week 5 | Week 6 | Week 7 | Week 8 | Week 9 |
|---|---|---|---|---|---|---|---|---|---|
| 6 (uninoculated negative control) | 10/10 (100%) | 10/10 (100%) | 10/10 (100%) | 10/10 (100%) | 10/10 (100%) | 10/10 (100%) | 10/10 (100%) | 10/10 (100%) | 10/10 (100%) |

Histopathological evaluation of tissues (kidney, spleen, liver, heart and brain) revealed lesions which were consistent with Marek's disease in surviving birds from the infected groups. No such lesions were seen in birds from the cell control or negative control groups.

For virus reisolation, between 0.5 and 2ml of chicken blood was collected in heparinized tubes by wing vein puncture from each chick on day 14 post-inoculation. The blood from each experimental group was pooled and centrifuged. The buffy coat cells were removed from each tube and used to inoculate DEF monolayers. At day 4 post inoculation the cells were fixed with 80% acetone and prepared for IFA. The cell control and negative control groups were negative by IFA for MDV. The positive control, OU2. NLFK clone 3G4. and NLFK clone 9 groups were positive for MDV by IFA.

EXAMPLE 6

Two additional isolates of MDV-1, designated 652 and 584A. were adapted to growth in the 3G4 clone of NLFK cells. These isolates are more recent and more virulent then the Md5 isolate (Witter, R. L., Avian Dis., V. 41, pp. 149–163 (1997)]. The methods used to adapt these isolates to growth in 3G4 cells are essentially identical to those described in Example 3 for adaptation of isolate Md5 to growth in various clones of NLFK cells.

EXAMPLE 7

Preparation of NLFK 3G4 MDV gH Expressing
Cell Line Preparation of pCR3.1 gH Construct The 2.6 kb Glycoprotein H (gH) gene from Marek's Disease Virus strain MD5 was isolated 3 by polymerase chain reaction (PCR) and cloned into pCR2 TA cloning (TA cloning vector, available from Invitrogen Inc., U.S.A., catalogue number K2000-1) by polymerase chain reaction (PCR) using a commercially available PCR regent system (GIBCO-Life Technologies, cat No. 10198-018), using an upper PCR primer 5'-GGGGG TACCA AGUG CATTG GATGG CTACA TA-3' (SEQ ID NO: 3) and a lower PCR primer 5'-GGGGC TAGCT TAAAG ATCGT CGTAC AGGCT CAA-3(SEQ ID NO: 4). The gH gene can be sequenced using known techniques. The sequence for the gH gene is described by Scott et al., J. Gen. Virol. vol. 74. pp. 1185–1190. (1993).

Figure 1:
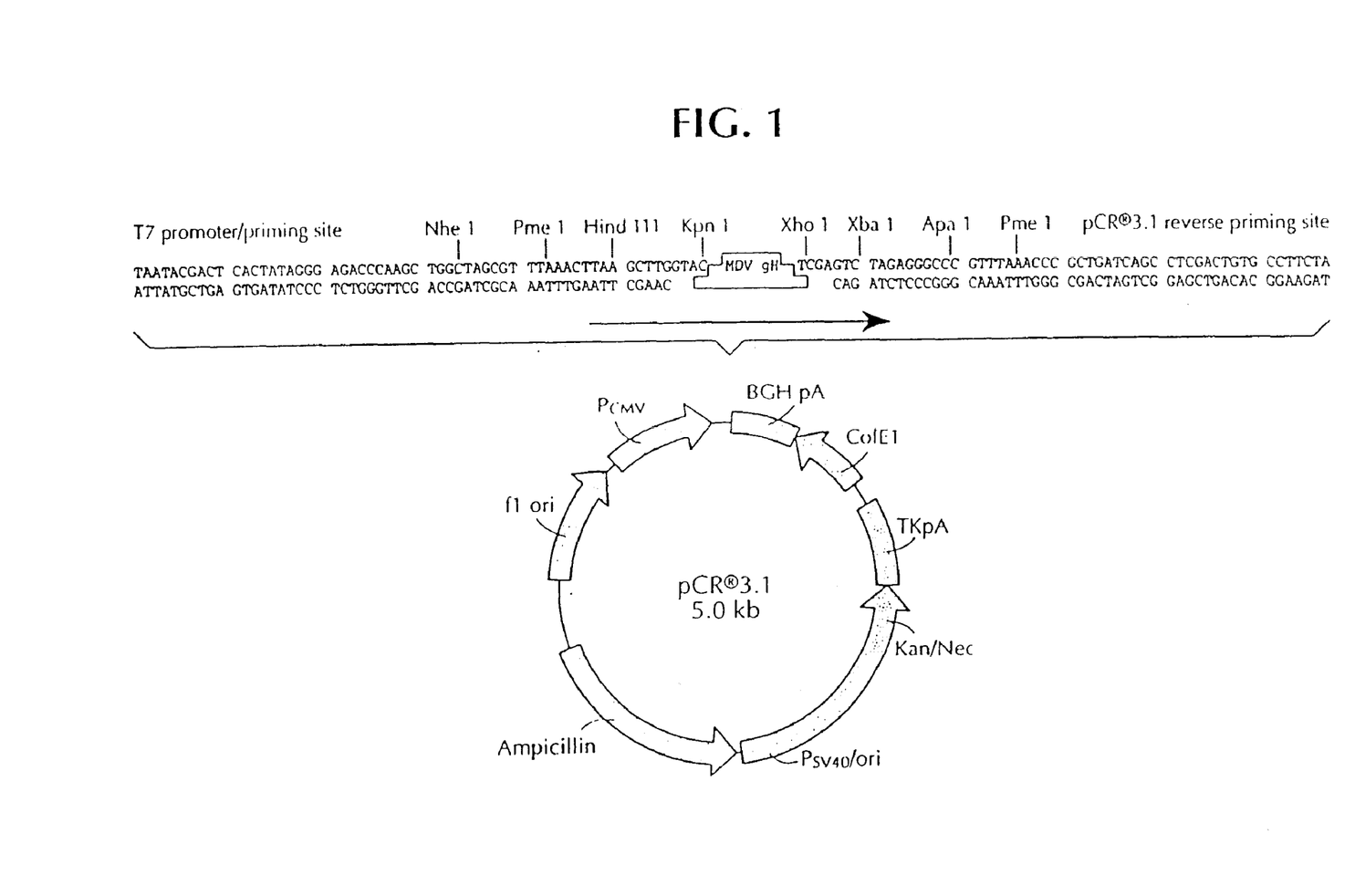
FIG. 1 describes the insertion of the Marek's Disease Virus-gH gene into the map of the pCR 3.1 vector (SEQ ID NO: 9–12).
Figure 2:
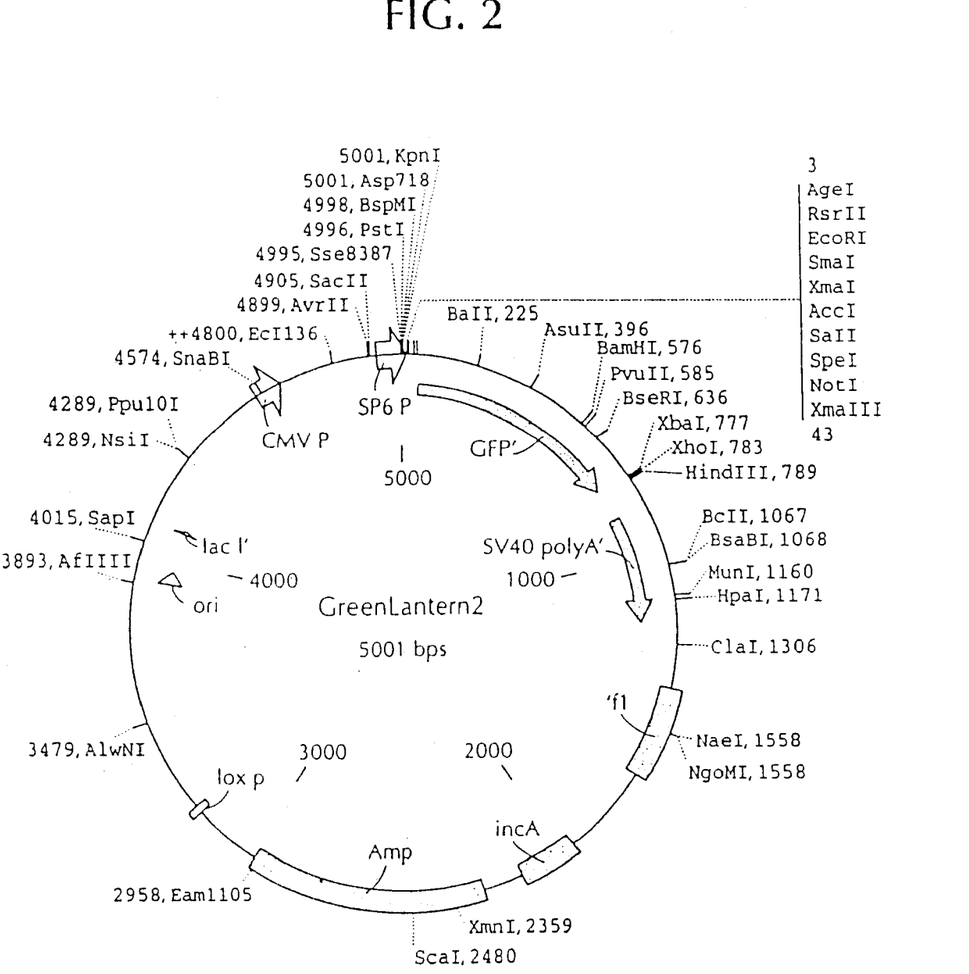
FIG. 2 is a map of the pGreen Lantern2 plasmid.
Figure 3:
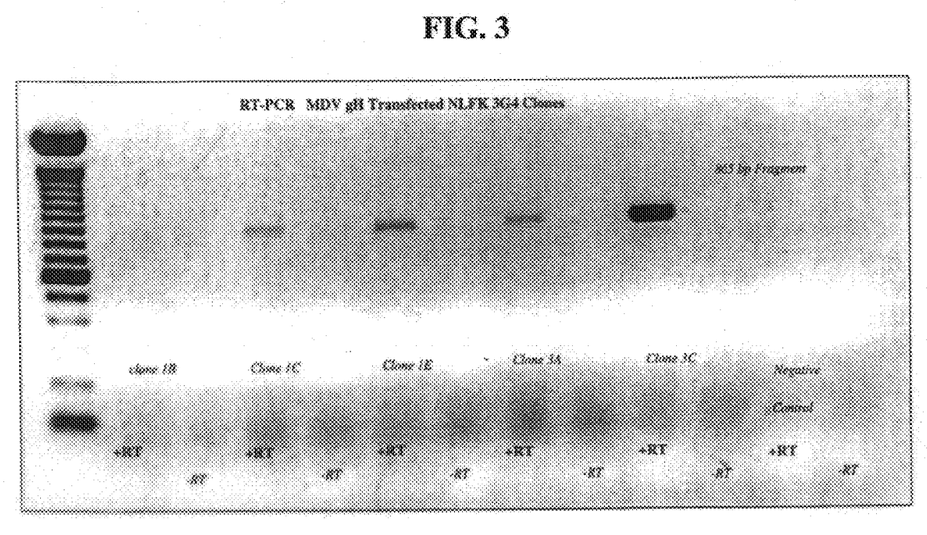
FIG. 3 describes the reverse transcriptase PCR analysis of Marek's Disease Virus gH transfected NLFK 3 G4 cells.

The MDV gH gene was then subcloned into pCR3.1 vector (available from Invitrogen Inc., U.S.A., Catalog Number K3000-01) utilizing the Kpnl and Xhol sites in the multiple cloning site (see FIG. 1). The vector pCR3.1 is a eukaryotic expression vector containing cytomegalovirus (CMV) immediate-early promoter for efficient mammalian expression and the neomycin resistance gene to allow positive selection for cells that contain the vector. The vector pCR3.1 is characterized by the following: CMV promoter bases 1–596; putative transcriptional start bases 520–625; 17 promoter/priming site bases 638–657; multiple cloning site bases 670–785; pCR3.1 reverse priming site bases 797415; BGH polyadenylation site bases 796–1010; ColE1 oring bases 1100–1773; SV40 promoter and origin bases 3178–3515; pGreenLantern-2 plasmid, available from GIBCO-Life Technologies. U.S.A (see FIG. 2). The 5 flanking region of MDV-1 gH is available from GeneBank, U.S.A. contains the TK gene at position 894 to 1925. The pGreenLantern-2 plasmid has the gene encoding for the jellyfish green fluorescence protein (gfp) which is used as the marker protein in the process of generating gH-deleted recombinant virus. The Nsi1 site of pGreenLantern-2, upstream of the CMV promoter for the green fluorescence protein gene, is treated with T4 polymerase to create a blunt-end for ligating with the 5' gH flanking region containing Pme 1 ends.

A plasmid was obtained from Dr. Meihan Nonoyama of the Tampa Bay Research Institute FL, U.S.A. containing the MDV-1 BamH1 fragment F. which includes the gH 3' flanking region [Fukuchi et at, J. Virol. 102–109, (1984)]. The DNA sequence of about a 2.4 kb region (referred to herein as the 3"flanking region") is shown in SEQ ID No: 2 The MDV-1 gH 3 flanking region was obtained by PCR cloning (Upper primer: 5'- AAGAT TTTTC CCAAG TCC-3' (SEQ ID NO: 5). Lower primer 5'-TCGTC GMTA ATGTG ATC-3) and doned into the above mentioned pGreenLantern-2 plasmid which has the MDV.1 5' flanking region inserted at the Nsi1 site. The 3 flanking region was inserted into the Nael site, downstream of the whole green fluorescence protein gene.

This plasmid which has green fluorescence protein gene flanked by the 5' and 3' flanking regions of MDV-1 gH is transfected into the gH-producing 3G4 cell line infected with MDV-1. Green virus plaques are selected under the ultraviolet microscope and purified from parental MDV-1 viruses. The resulting new recombinant virus has the gH gene deleted and replaced by the gene encoding for the green fluorescence protein.

In a second recombination step to remove the green fluorescence protein gene from the gH gene deleted virus, on can optionally insert heterologous genes from viruses other than MDV. Such as, for example, the chicken interferon gene, Newcastle disease virus, or infection bursal disease viruses etc., which can replace the green fluorescence protein gene. The presence of white virus plaques in contrast to parental green plaques, contain the new recombinant MDV-1 virus in which the gH gene is deleted and the green fluorescence protein gene removed A number of references have been cited and the entire disclosure of which are incorporated herein by reference.

The present invention is not to be limited in scope by the specific embodiments described which are intended as single illustrations of individual aspects of the invention, and functionally equivalent methods and components are with in the scope of the invention. Indeed various modifications of the invention, in addition to those shown and described

What is claimed is:

1. A method for producing a MDV which comprises culturing a continuous feline kidney cell line infected or transfected with nucleotide sequences encoding the MDV; wherein the MDV is used for the preparation of a vaccine capable of inducing protection against disease in avians, wherein the disease is the result of an infection by a virus selected from MDV, New Castle Disease Virus, Infectious Bronchitits Virus, Chicken Anemia Virus, Infectious Laryngotracheitis Virus, Retriculoendotheliosis Virus or Avian Influenza Virus; wherein the nucleotide sequences encode a naturally occurring MDV or a recombinant MDV; wherein the naturally occurring MDV is a virus selected from the group consisting of serotype 1, serotype 2 and serotype 3, taken singly or in any combination thereof, wherein if the MDV is a recombinant molecule, it comprises the nucleic acid sequence of MDV and optionally at least one heterologous gene or fragment thereof inserted into said nucleic acid sequence of MDV and further comprises the nucleic acid sequence of MDV from which one or more genes, regulatory genetic elements, or fragment thereof has been deleted, wherein if the deleted gene is essential for replication, said gene is gH.

2. A continuous mammalian cell line containing nucleotide sequences encoding a naturally occurring MDV or a recombinant MDV genome; wherein the cell line is a feline kidney cell line infected or transfected with MDV; wherein the MDV is used for the preparation of a vaccine capable of inducing protection against disease in avians, wherein the disease is the result of an infection by a virus selected from MDV, New Castle Disease Virus, Infectious Bronchitits Virus, Chicken Anemia Virus, Infectious Laryngotracheitis Virus, Retriculoendotheliosis Virus or Avian Influenza Virus; wherein the naturally occurring MDV is a virus selected from the group consisting of serotype 1, serotype 2 and serotype 3, taken singly or in any combination thereof;

wherein if the MDV is a recombinant molecule, it comprises the nucleic acid sequence of MDV and optionally at least one heterologous gene or fragment thereof inserted into said nucleic acid sequence of MDV and further comprises the nucleic acid sequence of MDV from which one or more genes, regulatory genetic elements, or fragment thereof has been deleted, wherein if the deleted gene is essential for replication, said gene is gH.

3. The cell line of claim 2 wherein the MDV is MDV-1 strain Md5.

* * * * *